United States Patent
McDonald et al.

(10) Patent No.: US 9,993,452 B2
(45) Date of Patent: Jun. 12, 2018

(54) COMPOSITIONS AND METHODS FOR TREATMENT OF INFLAMMATION

(71) Applicant: Vireo Systems, Inc., Madison, TN (US)

(72) Inventors: Thomas McDonald, Omaha, NE (US); Kristen Drescher, Omaha, NE (US)

(73) Assignees: Vireo Systems, Inc., Madison, TN (US); Creighton University, Omaha, NE (US)

( * ) Notice: Subject to any disclaimer, the term of this patent is extended or adjusted under 35 U.S.C. 154(b) by 0 days. days.

(21) Appl. No.: 14/960,806

(22) Filed: Dec. 7, 2015

(65) Prior Publication Data

US 2016/0175272 A1 Jun. 23, 2016

Related U.S. Application Data

(60) Provisional application No. 62/088,248, filed on Dec. 5, 2014.

(51) Int. Cl.

| *A61K 31/415* | (2006.01) |
| *A61K 31/19* | (2006.01) |
| *A61K 31/198* | (2006.01) |
| *A61K 9/00* | (2006.01) |
| A61K 31/4168 | (2006.01) |
| A61K 31/417 | (2006.01) |

(52) U.S. Cl.
CPC .......... *A61K 31/198* (2013.01); *A61K 9/0014* (2013.01); *A61K 31/417* (2013.01); *A61K 31/4168* (2013.01)

(58) Field of Classification Search
CPC .......................... A61K 31/4168; A61K 31/417
USPC ................................................. 514/388, 570
See application file for complete search history.

(56) References Cited

U.S. PATENT DOCUMENTS

| 3,385,886 | A | * | 5/1968 | Nicholson | C07C 29/147 514/916 |
| 3,933,797 | A | | 1/1976 | Hamanaka | 260/239.1 |
| 5,627,172 | A | | 5/1997 | Almada et al. | 514/120 |
| 5,773,473 | A | | 6/1998 | Green et al. | 514/565 |
| 5,817,329 | A | | 10/1998 | Gardiner | 424/439 |
| 5,965,596 | A | | 10/1999 | Harris et al. | 514/400 |
| 5,973,005 | A | | 10/1999 | D'Amelio, Sr. et al. | 514/565 |
| 6,136,339 | A | | 10/2000 | Gardiner | 424/439 |
| 6,168,802 | B1 | | 1/2001 | Howard et al. | 424/439 |
| 6,339,819 | B1 | | 1/2002 | Huppenthal et al. | 712/16 |
| 6,620,425 | B1 | | 9/2003 | Gardiner | 424/439 |
| 6,784,209 | B1 | | 8/2004 | Gardiner et al. | 514/565 |
| 6,897,334 | B2 | | 5/2005 | Vennerstrom | 560/169 |
| 7,608,641 | B2 | | 10/2009 | Miller et al. | 514/565 |
| 8,026,385 | B2 | | 9/2011 | Miller et al. | 560/169 |
| 8,354,450 | B2 | | 1/2013 | Miller et al. | 514/565 |
| 8,962,685 | B2 | | 2/2015 | Miller | A23K 1/609 |
| 2002/0150627 | A1 | | 10/2002 | Stout et al. | 424/601 |
| 2009/0253797 | A1 | | 10/2009 | Miller et al. | 514/565 |
| 2010/0204204 | A1 | | 8/2010 | Zaworotko et al. | 514/212.03 |

FOREIGN PATENT DOCUMENTS

| CN | 101407478 | 4/2009 | |
| WO | WO 0222135 | 3/2002 | |
| WO | WO 2013158319 A1 * | 10/2013 | ............. A61K 47/44 |

OTHER PUBLICATIONS

Madan et al., "Effect of Creatinine on Various Experimentally Induced Inflammatory Models", Indian Journal of Physiology and Pharmacology, vol. 23, No. 1, pp. 1-7 (1979).*
Miller, D. Oral bioavailability of creatine supplements: Is there room for improvement? Annual Meeting of the International Society of Sports Nutrition, 2009.
Cross, Comparison or Creatine HCl solution stability to Creatine Monohydrate? Feb, 23, 2010. [Retrieved from the Internet Feb. 12, 2012: URL:http://web.archive.org/web/20100911070855/http://www.concret.com/downloads/CRT_HCl_solutionstability.pdf]; p. 1.
Brosnan JT et al., Ann Rev Nutr 27: 241-261 (2007).
Greenhaff P, J Nutr Biochem 8: 610-618 (1997).
Wyss M et al., Physiol Rev 80: 1107-1213 (2000).
Williams MH et al., J Am Coll Nutr 17: 216-234 (1998).
Santos RV, et al. Life Sci 75: 1917-1924 (2004).
McDonald TL et al., J Antibiot (Tokyo) 65: 153-156 (2012).
Smithee et al., J Microbiol Meth 105: 155-161 (2014).

* cited by examiner

*Primary Examiner* — Kevin E Weddington
(74) *Attorney, Agent, or Firm* — Bradley Arant Boult Cummings LLP

(57) ABSTRACT

The present invention is directed to novel anti-inflammatory immunomodulators including creatinine or a creatinine salt, for example, creatinine hydrochloride. The present invention is also directed to methods for treating inflammation and inducing an immunomodulatory response. In particular, the anti-inflammatory immunomodulators are useful for treating an inflammatory condition or an autoimmune disease.

10 Claims, 4 Drawing Sheets

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtggcaaagt ggagattgtt g                                              21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cattctcggc cttgactgtg                                                20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acgtggaact ggcagaagag                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctcctccact tggtggtttg                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic -continued

```
          primer

<400> SEQUENCE: 5
tggtctcctc tgacttcaac                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cctgttgctg tagccaaatt                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caagcctgta gcccatgttg                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agaggacctg ggagtagatg                                              20
```

COMPOSITIONS AND METHODS FOR TREATMENT OF INFLAMMATION

CROSS-REFERENCE TO RELATED APPLICATION

This application claims the benefit of U.S. Provisional Application No. 62/088,248, filed Dec. 5, 2014, the entire disclosure of which is incorporated by reference herein.

REFERENCE TO A SEQUENCE LISTING SUBMITTED VIA EFS-WEB

The content of the ASCII text the of the Sequence Listing named "20160307_34555_037_Sequence_Listing" which is 2.05 KB in size was created on 7 Mar. 2016 and electronically submitted via EFS-Web on 10 Mar. 2016 is incorporated herein by reference in its entirety.

FIELD OF THE INVENTION

The present invention is directed to novel anti-inflammatory immunomodulators including creatinine or a creatinine salt, for example, creatinine hydrochloride. The present invention is also directed to methods for treating inflammation and inducing an immunomodulatory response. In particular, the anti-inflammatory immunomodulators are useful for treating an inflammatory condition or an autoimmune disease.

BACKGROUND OF THE INVENTION

Creatinine is the naturally occurring breakdown product of creatine. Creatine is an organic acid that is synthesized in the liver and kidneys from arginine, glycine, and methionine (Brosnan J T et al., Ann Rev Nutr 27: 241-261 (2007); Greenhaff P, J Nutr Biochem 8: 610-618 (1997); Wallimann et al., Amino Acids 40: 1271-1296 (2011)). In the kidneys arginine and glycine undergo an aminotransferase producing guanidinoacetic acid that acquires a methyl group from methionine during methytransferase in the liver (Brosnan J T et al., Ann Rev Nutr 27: 241-261 (2007); Greenhaff P, J Nutr Biochem 8: 610-618 (1997); Wyss M et al., Physiol Rev 80: 1107-1213 (2000)). The majority (e.g., 95%) of all creatine in the body is found in skeletal muscle, and plays a pivotal role in energy homeostasis (Greenhaff P, J Nutr Biochem 8: 610-618 (1997); Williams M H et al., J Am Coll Nutr 17: 216-234 (1998)). In the muscle, creatine converts into phosphocreatine by creatine kinase, which is utilized to increase the ATP pool during explosive movements such as wrestling or jumping. Creatine is non-enzymatically converted into creatinine (Wyss M et al., Physiol Rev 80: 1107-1213 (2000); Santos R V, et al. Life Sci 75: 1917-1924 (2004)). Creatinine diffuses out of the muscle into the blood and is excreted in the urine. Blood creatinine levels are used as an indicator of renal function. For instance, 50-100 µM of creatinine in the blood is considered normal (Brosnan J T et al., Ann Rev Nutr 27: 241-261 (2007); McDonald T L et al., J Antibiot (Tokyo) 65: 1:53-156 (2012)). Creatinine has thought to have been an inert waste product with no active function; however, recent studies have challenged this dogma.

Previous works studying the potential of creatinine as an immunomodulator have found that creatinine (and its derivatives such as creatinine HCl) possesses biological activity. Indeed, one study conducted by Madan et al. (1979) involved injecting rats with different doses of creatinine and a variety of inflammatory agents (e.g., 5-hydroxytryptamine creatine sulfate, nystatin, and carrageen) to induce acute or chronic inflammation (Indian J Physiol Pharmacol 1-7). Edema was measured in all rats and was decreased with the presence of creatinine. In this study, creatinine acted as an anti-inflammatory agent against acute and chronic inflammation in rats. Another study done by Leland et al. (2011), examined the effects of creatine and creatinine HCl on molecules associated with recognizing pathogen-associated molecular patterns ("PAMPs") in mouse macrophages (Int Immunopharm 11: 1341-1347). In this study, mRNA levels were assayed for four toll-like receptors (TLRs)—TLR-2, TLR-3, TLR-4, and TLR-7. Transcript levels for all four TLRs were reduced following exposure of the cells to creatinine HCl. No alterations in cell death were observed. This study suggested that creatinine may have the ability to dampen the innate immune response.

Furthermore, another study demonstrated the ability of creatinine HCl to suppress bacterial replication. Addition of creatinine HCl to a growth medium decreased a wide array of Gram negative and Gram positive bacteria as well as drug resistant *Staphylococcus aureus* ("MRSA") and vancomycin resistant *Enterococcus faecium* ("VRE"). Although the mechanism was not clearly defined, the addition of a proton pump inhibitor decreased the concentration of creatinine HCl necessary to kill cells, suggesting the mechanism of action was related to the bacterial cells' capacity to pump out protons (McDonald T L et al., J Antibiot (Tokyo) 65: 153-156 (2012)). A subsequent study from the same group showed that creatinine HCl does not affect the growth of fungi; an observation that was used to demonstrate that creatinine HCl could be used as a novel additive in fungal growth media to permit fungi to grow efficiently without bacterial contamination (Smithee et al., J Microbiol Meth 105: 155-161 (2014)). Such an effect could aid in the identification of novel antibiotic-producing fungi from environmental sources.

Collectively, these studies indicate creatinine is not an inert waste product of creatine, and instead has an active function particularly when protonated. However, these studies present only general findings. The full effects of creatinine remain unknown and are not commonly understood by those of ordinary skill in the art. Accordingly, there remains a need in the art to further understand and appreciate how creatinine works within the body and the effects that may result therefrom.

SUMMARY OF THE INVENTION

The present invention is directed to a method for treating an inflammatory condition in a patient, including administering an effective amount of an anti-inflammatory agent to the patient, wherein the anti-inflammatory agent includes a creatinine salt, for example, creatinine hydrochloride, and wherein levels of tumor necrosis factor alpha in the patient are reduced by at least 40 percent when compared to levels prior to administration of the anti-inflammatory agent. In one embodiment, the inflammatory condition is selected from the group consisting of rheumatoid arthritis, osteoarthritis, psoriatic arthritis, psoriasis, and inflammatory bowel disease. For example, the inflammatory condition may be rheumatoid arthritis. In another embodiment, the anti-inflammatory agent is administered to the patient as a topical formulation. The topical formulation may include the anti-inflammatory agent in an amount of about 10 percent by weight to about 40 percent by weight. In still another embodiment, the anti-inflammatory agent is administered in conjunction with at least one other compound selected from the group consisting of a homeopathic compound, a co-medication, a nutraceutical, a plant extract, a herbal preparation, a cosmetic agent, a pharmaceutical, or combinations thereof.

The present invention is also directed to a method for treating inflammation associated with an autoimmune disease in a patient, including administering a topical formulation to an inflamed area of the patient, wherein the topical formulation includes an effective amount of creatinine hydrochloride. In one embodiment, the effective amount of creatinine hydrochloride is about 10 percent by weight to about 40 percent by weight, for example, about 15 percent by weight to about 35 percent by weight. In another embodiment, the topical formulation is an ointment, lotion, cream, gel, adhesive patch, or a wrap. For instance, the adhesive patch or wrap includes a controlled release system for administration of the topical formulation. In still another embodiment, the autoimmune disease is selected from the group consisting of rheumatoid arthritis, inflammatory bowel disease, and multiple sclerosis.

The present invention is further directed to a method of inducing an immunomodulatory response in a patient in need thereof, including administering to the patient in need thereof an immunomodulating agent in an amount effective to produce an immunomodulatory effect, wherein the immunomodulating agent includes creatinine hydrochloride. In one embodiment, the immunomodulating agent is administered to the patient in an amount of about 10 percent by weight to about 40 percent by weight, for example, about 15 percent by weight to about 35 percent by weight. In another embodiment, the immunomodulating agent is administered to the patient via a topical formulation, for instance, an ointment, lotion, cream, gel, adhesive patch, or a wrap. In still another embodiment, the immunomodulating agent is administered in conjunction with at least one other compound selected from the group consisting of a homeopathic compound, a co-medication, a nutraceutical, a plant extract, a herbal preparation, a cosmetic agent, a pharmaceutical, or combinations thereof. In yet another embodiment, the immunomodulating agent may further include at least one of creatinine, creatinine nitrate, creatinine malate, creatinine gluconate, and creatinine citrate.

BRIEF DESCRIPTION OF THE DRAWINGS

Further features and advantages of the invention can be ascertained from the following detailed description that is provided in connection with the drawing(s) described below.

DETAILED DESCRIPTION OF THE INVENTION

Figure 1A:
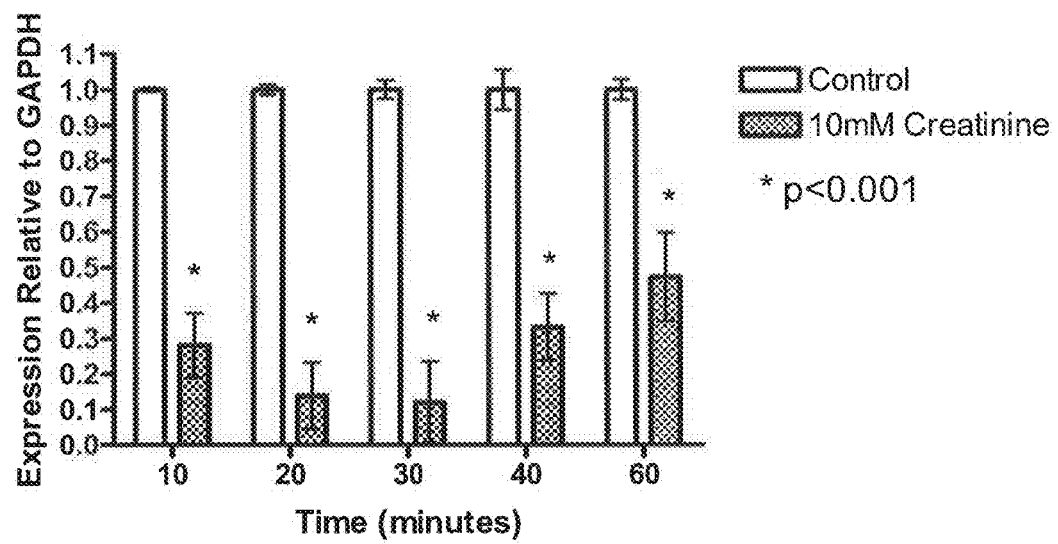
FIG. 1A is a graphical representation illustrating TNF-α mRNA expression following treatment of mouse macrophages with creatinine HCl.

The present invention is directed to methods for treating inflammation and the anti-inflammatory agents and compositions useful in the method. In particular, the present invention provides novel anti-inflammatory immunomodulators including creatinine and its salts, for example, creatinine hydrochloride. In one embodiment, the anti-inflammatory immunomodulators are useful for treating an inflammatory condition or an autoimmune disease. In another embodiment, the anti-inflammatory immunomodulators are useful for inducing an immunomodulatory response.

The inventors of the present invention surprisingly discovered that creatinine, once believed to be an inert waste product, possesses anti-inflammatory properties. Indeed, the inventors discovered that creatinine and its salts, for example, creatinine hydrochloride ("creatinine HCl"), act as anti-inflammatory immunomodulators in suppressing tumor necrosis factor-α ("TNF-α") expression. TNF-α is a pro-inflammatory cytokine that is secreted by macrophages and CD 4$^+$ T cells, as well as other cell types, during an immune response to initiate inflammation, TNF-α is one of the critical cytokines that mediate joint damage and destruction due to its activities on many cells in the joint as well as effects on other organs and body systems. Without being bound by any particular theory, it is believed that creatinine and its salts down regulate both mRNA and protein levels of TNF-α during an inflammatory response. By reducing TNF-α levels, creatinine and creatinine salts inhibit the inflammatory response.

Additionally, creatinine and its salts may act as anti-inflammatory immunomodulators in suppressing interleukin 6 ("IL-6"). IL-6 is an interleukin that acts as a pro-inflammatory cytokine. IL-6 is secreted by T cells and macrophages to stimulate an immune response, for example, during infection and after trauma. It is believed that creatinine and its salts suppress IL-6 during an inflammatory response.

In one embodiment, the compositions of the present invention have been found to down regulate TNF-α mRNA levels in both mouse and human macrophage cells. The compositions of the present invention have been found to reduce TNF-α mRNA levels in mouse and human macrophage cells by about 40 percent or more when compared to levels prior to administration of the compositions of the present invention. In another embodiment, the compositions of the present invention have been found to reduce TNF-α mRNA levels in mouse and human macrophage cells by about 50 percent or more when compared to levels prior to administration of the compositions of the present invention. In still another embodiment, the reduction in TNF-α mRNA levels in mouse and human macrophage cells is about 60 percent or more when compared to levels prior to administration of the compositions of the present invention. In yet another embodiment, the effects of the compositions of the present invention result in a reduction of TNF-α mRNA levels in mouse and human macrophage cells of about 70 percent or more. In still another embodiment, the effects of the compositions of the present invention result in a reduction of TNF-α mRNA levels in mouse and human macrophage cells of about 80 percent or more. Indeed, the compositions of the present invention have been found to reduce TNF-α mRNA levels in mouse and human macrophage cells by as much as 90 percent.

For example, the creatinine salt, creatinine HCl, has been found to decrease TNF-α mRNA expression in mouse macrophage cells. In one embodiment, a concentration of about 10 mM of creatinine HCl may result in a decrease of TNF-α mRNA expression in mouse macrophages of about 50 percent or more after a time period of about 10 minutes to about 60 minutes post-treatment. In another embodiment, a concentration of about 10 mM of creatinine HCl results in a decrease of TNF-α mRNA expression in mouse macrophages of about 72 percent or more after a time period of about 10 minutes post-treatment. In still another embodiment, administration of the compositions of the present invention reduces TNF-α mRNA expression in mouse macrophages by as much as 87 percent with creatinine HCl concentrations of about 10 mM after a time period of about 20 minutes post-treatment.

Similarly, in another embodiment, creatinine HCl has been found to reduce TNF-α mRNA expression in human macrophage cells. For instance, a concentration of about 10 mM of creatinine HCl may result in a decrease of TNF-α mRNA expression in human macrophages of about 20 percent or more after a time period of about 10 minutes to about 60 minutes post-treatment. In another embodiment, administration of the compositions of the present invention reduces TNF-α mRNA expression in human macrophages by about 50 percent or more with creatinine HCl concentrations of about 10 mM after a time period of about 10 minutes post-treatment. In still another embodiment, administration of the compositions of the present invention reduces TNF-α mRNA expression in human macrophages by about 60 percent or more with creatinine concentrations of about 10 mM after a time period of about 10 minutes post-treatment.

In another aspect of the invention, the compositions of the present invention have been found to decrease TNF-α mRNA levels in human T cells. The compositions of the present invention have been found to reduce TNF-α mRNA levels in human T cells by about 40 percent or more when compared to levels prior to administration of the compositions of the present invention. In another embodiment, the reduction in TNF-α mRNA levels in human T cells is about 50 percent or more when compared to levels prior to administration of the compositions of the present invention. In still another embodiment, the effects of the compositions of the present invention result in a reduction of TNF-α mRNA levels in human T cells of about 60 percent or more. In yet another embodiment, the effects of the compositions of the present invention result in a reduction of TNF-α mRNA levels in human T cells of about 70 percent or more. Indeed, the compositions of the present invention have been found to reduce TNF-α mRNA levels in human T cells by as much as 75 percent.

For example, following exposure to 10 mM of creatinine HCl, TNF-α mRNA levels in human T cells are reduced by about 40 percent or more when compared to the control. In one embodiment, following exposure to 10 mM of creatinine HCl, TNF-α mRNA levels in human T cells are reduced by about 50 percent or more when compared to the control. In another embodiment, TNF-α mRNA levels in human T cells are reduced by about 60 percent or more following exposure to 10 mM of creatinine HCl. In still another embodiment, TNF-α mRNA levels in human T cells are reduced by about 70 percent or more following exposure to 10 mM of creatinine HCl. Indeed, administration of the compositions of the present invention reduces mRNA levels in human T cells by as much as 75 percent with creatinine HCl concentrations of about 10 mM after a time period of 20 minutes post-treatment.

In another embodiment of the present invention, the inventors surprisingly discovered that alterations in TNF-α mRNA expression after exposure to the compositions of the present invention result in alterations in TNF-α protein expression. Indeed, the compositions of the present invention have been found to reduce TNF-α protein expression in cells. For example, following exposure to 10 mM of creatinine HCl, mouse macrophage cells displayed lower protein detection and demonstrated reduced TNF-α protein expression after time periods of 24 hours and 48 hours post-treatment when compared to the control.

Similarly, the inventors surprisingly discovered that alterations in TNF-α mRNA expression after exposure to creatine monohydrate result in alterations in TNF-α protein expression. Like creatinine creatine monohydrate has been found to reduce TNF-α protein expression in cells. For example, following exposure to 10 mM of creatine monohydrate, mouse macrophage cells displayed lower TNF-α signals and demonstrated reduced TNF-α protein expression after time periods of 24 hours and 48 hours post-treatment when compared to the control. In this aspect, it is believed that the decrease in TNF-α signal following treatment with creatine monohydrate is due to the quick hydrolyzation of creatine into creatinine.

Compositions of the Invention

In one embodiment, the compositions of the present invention include creatinine. For example, the compositions according to the invention may include a compound having the structure of formula (I):

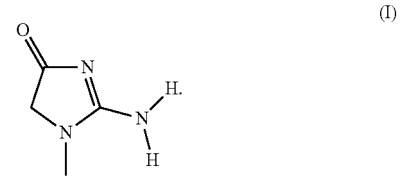

In another embodiment, the compositions of the present invention include a creatinine salt. For example, creatinine salts contemplated by the present invention include, but are not limited to, creatinine HCl, creatinine nitrate, creatinine malate, creatinine gluconate, creatinine zinc chloride, and creatinine citrate.

In still another embodiment, the compositions according to the invention include creatinine HCl. For example, the compositions according to the invention may include a compound having the structure of formula (II):

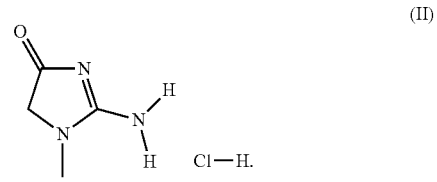

In yet another embodiment, the compositions of the present invention may include a combination of creatinine and at least one creatinine salt. For example, the compositions of the present invention may include creatinine and creatinine HCl. In another embodiment, the compositions of the present invention may include a combination of two or more creatinine salts. For instance, the compositions of the present invention may include creatinine HCl and creatinine nitrate.

The creatinine and creatinine salts of the present invention may be produced by any suitable method known to one of ordinary skill in the art. Preparations of the creatinine and creatinine salts for use with the present invention are preferably at least about 80 percent pure, preferably at least about 95 percent pure, more preferably at least about 97 percent pure, and even more preferably at least about 99 percent pure. The term "pure" as used herein refers to the lack of impurities in the preparation.

The creatinine and creatinine salts of the present invention may be blended in a composition with at least one other compound. In one embodiment, the at least one other compound includes a homeopathic compound, a co-medication, a nutraceutical, a plant extract, a herbal preparation, a cosmetic agent, a pharmaceutical, or combinations thereof. In another embodiment, the creatinine or creatinine salt is present in a composition or blend with at least two other compounds.

For example, the creatinine or creatinine salt may be combined with another ingredient in a solid dosage form. In one embodiment, the creatinine or creatinine salt may be present in a composition with other forms of creatine. The creatinine or creatinine salt may be combined with creatine monohydrate, creatine esters, creatine pyruvate, creatine phosphate, creatine alpha ketoglutarate, creatine citrate, and combinations thereof. In this aspect of the present invention, where the creatinine or creatinine salt is present in a composition or blend with at least one other compound, it is contemplated that the creatinine or creatinine salt will account for greater than 50 percent of the total weight of the composition. In another embodiment, the creatinine or creatinine salt may account for less than 50 percent of the total weight of the composition.

The compositions of the present invention may further include at least one of any suitable auxiliaries including, but not limited to, diluents, binders, stabilizers, buffers, salts, lipophilic solvents, preservatives, adjuvants or the like. Pharmaceutically acceptable auxiliaries are preferred. Pharmaceutically acceptable carriers may be routinely selected that are suitable for the mode of administration, solubility and/or stability of the compound.

Pharmaceutical excipients and additives useful in the present invention may also include, but are not limited to, proteins, peptides, amino acids, lipids, and carbohydrates. Suitable protein excipients include serum albumin such as human serum albumin (HSA), recombinant human albumin (rHA), gelatin, casein, and combinations thereof. Suitable amino acid components include, but are not limited to alanine, glycine, arginine, betaine, histidine, glutamic acid, aspartic acid, cysteine, lysine, leucine, isoleucine, valine, methionine, phenylalanine, aspartame, and combinations thereof. Suitable carbohydrate excipients include, but are not limited to monosaccharides such as fructose, maltose, galactose, glucose, D-mannose, sorbose, and combinations thereof; disaccharides, such as lactose, sucrose, trehalose, cellobiose, and combinations thereof; polysaccharides, such as raffinose, melezitose, maltodextrins, dextrans, starches, and combinations thereof; and alditols, such as mannitol, xylitol, maltitol, lactitol, xylitol, sorbitol (glucitol), myoinositol, and combinations thereof.

The composition may also contain pharmaceutically acceptable carriers such as coloring agents, emulsifying agents, suspending agents, ethanol, EDTA or similar chelating agents, citrate buffer, flavoring, water, and combinations thereof. In addition, the compositions may also include a buffer or a pH adjusting agent. Suitable buffers include, but are not limited to, organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

Moreover, the compositions may include polymeric excipients/additives such as polyvinylpyrrolidones, fleas, dextates, polyethylene glycols, flavoring agents, anti-microbial agents, sweeteners, antioxidants, anti-static agents, surfactants, lipids, steroids, and chelating agents.

Methods of Administration

The compositions of the invention may be administered to any patient that can experience the beneficial effects of the compounds of the invention. A "patient" may include humans and non-humans such as canines, pets, and farm animals.

The present invention provides methods for treating inflammation. The terms "treatment," "treating," and "treat, are used herein to refer generally to obtaining a desired pharmacological and/or physiological effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

In this aspect of the invention, the compositions of the present invention may be used to treat any type of condition involving an inflammation component. As will be apparent to one of ordinary skill in the art, an "inflammation component" includes any type of localized protective response elicited by injury or destruction of tissues, which serves to destroy, dilute, or wall off both the injurious agent and the injured tissue. In one embodiment, the inflammatory condition is dermatological in nature. For example, the inflammatory condition may include rashes, contusions, or other conditions resulting from a direct immune attack on the dermis, such as in psoriasis, or from immune reactions to alterations or modifications of the dermis (chemical or other), such as in Arthus reactions or Delayed Type Hypersensitivities (DTH).

In one embodiment, the present invention contemplates treatment of inflammation associated with an inflammatory condition. For example, the present invention provides a method for treating an inflammatory condition in a patient including administering an effective amount of creatinine or creatinine salt to the patient. In one embodiment, the present invention provides a method for treating an inflammatory condition in a patient including administering an effective amount of creatinine HCl to the patient. Due to the ability of creatinine HCl to significantly reduce TNF-α levels in macrophages and T cells, the creatinine HCl of the present invention provides anti-inflammatory effects that aid in reducing the injury or destruction of tissues caused by inflammation.

In another embodiment, the present invention contemplates treatment of inflammation associated with an autoimmune disease. As used herein, an "autoimmune disease" refers to any disease in which the body produces antibodies that attack its own tissues, leading to the deterioration and in some cases to the destruction of such tissue. For example, in one embodiment, the present invention provides a method for treating an autoimmune disease in a patient including administering an effective amount of creatinine or creatinine salt to the patient. In another embodiment, the present invention provides a method for treating an autoimmune disease in a patient including administering an effective amount of creatinine HCl to the patient. Indeed, as it is known in the art, autoimmune diseases express an abundance of TNF-α. In suppressing the production of TNF-α, the creatinine HCl of the present invention provides anti-inflammatory effects towards the immune system in treating the autoimmune disease.

Examples of inflammatory conditions and autoimmune diseases contemplated for treatment with the compositions of the present invention include, but are not limited to, osteoarthritis, rheumatoid arthritis, psoriatic arthritis, psoriasis, inflammatory myopathies, inflammatory bowel disease such as Crohn's disease and ulcerative colitis, multiple sclerosis, pancreatitis, lupus, and fibromyalgia.

For example, in one embodiment, the compositions of the present invention may be used to treat rheumatoid arthritis. Rheumatoid arthritis is an inflammatory reaction in the synovium of joints associated with erosion of cartilage and bone. Symptoms of rheumatoid arthritis include swelling and stiffness of the joints which become harder to move. As discussed above, TNF-α plays a central role in regulating the inflammatory response. TNF-α is found in large quantities in the rheumatoid joint and is produced locally in the joint by synovial macrophages and lymphocytes infiltrating the joint synovium. Without being bound by any particular theory, the inventors discovered that the creatinine or creatinine salt of the present invention functions as an anti-inflammatory immunomodulator by suppressing the overreaction and production of TNF-α associated with rheumatoid arthritis. Through suppression of the pro-inflammatory cytokine, TNF-α, the creatinine or creatinine salt of the present invention, for example, creatinine HCl, decreases the production of pro-inflammatory cytokines which results in a decrease of rheumatoid arthritis symptoms and aiding towards joint protection. Indeed, the creatinine of the present invention may treat inflammation associated with rheumatoid arthritis by decreasing TNF-α production in the blood.

In another aspect, the present invention provides methods for inducing an immunomodulatory response. By the term, "immunomodulatory response," it is meant an adjustment or regulation of one or more immune functions. For example, in one embodiment, the present invention provides a method for inducing an immunomodulatory response in a patient in need thereof including administering to the patient creatinine or a creatinine salt in an amount effective to produce an immunomodulatory effect. In another embodiment, the present invention provides a method for inducing an immunomodulatory response in a patient in need thereof including administering to the patient creatinine HCl in an amount effective to produce an immunomodulatory effect. Indeed, the compositions of the present invention function as immunomodulators in weakening or modulating the activity of the immune system. By weakening or modulating the activity of the immune system, the compositions of the invention decrease the inflammatory response.

The methods of administration of the compositions described herein to the patient may vary. However, in one embodiment, the creatinine or creatinine salt of the present invention is administered to the patient via a topical application. The topical application of the creatinine or creatinine salt may be applied directly to an inflamed area. For example, the compositions of the present invention may be administered to the patient as ointments, lotions, creams, gels, controlled release systems such as adhesive patches for prolonged topical applications, and controlled release wraps for prolonged topical applications to larger muscle areas.

In one embodiment, the creatinine or creatinine salt is administered to the patient via a transdermal patch or wrap formulated to contain the creatinine or creatinine salt anti-inflammatory compound in an internal semi-solid reservoir surrounded on one side with a semi-permeable membrane for diffusion-controlled release onto intact skin. In another embodiment, the creatinine or creatinine salt may be dissolved or dispersed within a lipoidal liquid or semi-solid vehicle that is then impregnated or adsorbed into the wraps and patches.

In still another embodiment, the topical formulations of the present invention may further include penetrating agents, which may be employed to increase the bio-availability of the creatinine or creatinine salt across a membrane, enhancing the lipophilicity of the creatinine or creatinine salt. For example, lipophilic solvents and/or nonionic surfactants may be used to further promote absorption. In yet another embodiment, to facilitate transdermal absorption, the topical formulations may employ iontophoresis or sonophoresis.

As used herein, "effective amount" refers to the amount of the compound necessary or sufficient to treat inflammation or induce an immunomodulatory response. In order to treat inflammation or induce an immunomodulatory response via the topical formulations of the present invention, the topical formulations include an effective amount of creatinine or creatinine salt of about 1 percent by weight to about 40 percent by weight. In another embodiment, an effective amount of creatinine or creatinine salt may range from about 5 percent by weight to about 40 percent by weight. In still another embodiment, an effective amount of creatinine or creatinine salt may range from about 10 percent by weight to about 40 percent by weight. In yet another embodiment, an effective amount of creatinine or creatinine salt may range from about 15 percent by weight to about 35 percent by weight. Indeed, an effective amount of creatinine or creatinine salt may range from about 20 percent by weight to about 30 percent by weight.

In this aspect, the topical formulations may include an effective amount of creatinine or creatinine salt of about 10 mg/g to about 400 mg/g. In another embodiment, the effective amount of creatinine or creatinine salt may range from about 50 mg/g to about 400 mg/g. In still another embodiment, the effective amount of creatinine or creatinine salt may range from about 100 mg/g to about 400 mg/g. In yet another embodiment, the effective amount of creatinine or creatinine salt may range from about 150 mg/g to about 350 mg/g. In another embodiment, the effective amount of creatinine or creatinine salt may range from about 200 mg/g to about 300 mg/g.

While a topical application is preferred, the creatinine or creatinine salt of the present invention may also be provided in a liquid, gel, or powder form. For example, the creatinine or creatinine salt may be in the form of a powder suitable for mixing with water or other liquids. These formulations may be added into a beverage or may be provided as an ingredient premixed in a beverage. The creatinine or creatinine salt may also be administered as an elixir or as a solution formulation. In another embodiment, the creatinine or creatinine salt may be encapsulated or tableted for a solid oral dosage form. For example, when treating a patient, the creatinine or creatinine salt may be administered in the form of a pill, tablet, capsule, or gel capsule. In yet another embodiment, the creatinine or creatinine salt may be administered in the form of a nutritional or dietary supplement. In still another embodiment, the creatinine or creatinine salt may be administered in the form of a functional food, for example, a protein bar.

The creatinine or creatinine salt of the present invention may be administered in conjunction with at least one other compound or pharmaceutical agent in a variety of protocols for effective treatment. In one embodiment, the at least one other compound includes a homeopathic compound, a co-medication, a nutraceutical, a plant extract, a herbal preparation, a cosmetic agent, a pharmaceutical, or combinations thereof.

EXAMPLES

The following non-limiting examples are merely illustrative of the preferred embodiments of the present invention, and are not to be construed as limiting the invention, the scope of which is defined by the appended claims.

The following examples demonstrate the effects of creatinine HCl on the expression of tumor necrosis factor-alpha ("TNF-α"), a pro-inflammatory cytokine, in a mouse macrophage cell line (RAW 264.7), a human macrophage cell line (THP-1), and a human T cell line (Jurkat clone E.6). The cell lines were chosen to determine whether results were consistent between species and between different cell types. TNF-α is known to be secreted at high levels by macrophages and some $CD4^+$ T cells during a pro-inflammatory response. Using real-time RT-PCR and immunohistochemical staining, the results of the following examples demonstrate that creatinine HCl down regulates both mRNA and protein levels of TNF-α.

Experimental Methods

The mouse macrophage cell line, RAW 264.7 (American Tissue Type Culture Collection (ATCC); Manassas, Va.), was cultured in Dulbucco's modified Eagle's medium (DMEM; ATCC) supplemented with 10% heat inactivated fetal calf serum (PBS) (Invitrogen; Carlsbad, Calif.), 100 µg/ml streptomycin and 100 U/ml penicillin (Invitrogen), and 2 mM L-glutamine (Invitrogen). The human T cell line, Jurkat clone E6-1 (ATCC) was cultured in RPMI-1640 medium (Invitrogen) supplemented as described above. The human monocyte cell line, THP-1 (ATCC) was cultured much like the Jurkat cultures plus the addition of 1 mM sodium pyruvate (Gibco-Invitrogen). THP-1 cells were stimulated with 200 nM of phorbol 12-myristate 13-acetate (PMA; Sigma-Aldrich, St. Louis, Mo.) for 48 hours to differentiate the cells into macrophage-like cells. Cells were then washed three times every 24 hours with fresh medium.

Dose response experiments were performed following exposure of the RAW 264.7, Jurkat, and THP-1 cells to varying doses of creatinine HCl (MW1.49.58; Sigma-Aldrich). Control cultures contained no creatinine HCl, only growth medium. A dose of 10 mM creatinine HCl was chosen for use in these studies. The 10 mM concentration is physiologically relevant to individuals supplementing with 5 grams of creatine for their regimen and then converted into creatinine.

RAW, Jurkat, and THP-1 cells were treated in 6-well plates at 80-90% confluent ($4.14 \times 10^6$ cells/ml, $2.6 \times 10^7$ cells/ml, and $5.26 \times 10^5$ cells/ml, respectively). All cells were lysed in 1 ml of Trizol (Invitrogen). After homogenization, chloroform was added to samples and nucleic acids extracted per the manufacturer's instructions. Nucleic acids were precipitated with isopropyl alcohol (Fisher, Pittsburgh, Pa.). Following centrifugation, the resulting pellets were washed with 75% ethanol and air dried. RNA was resuspended in 50 µl of UltraPure distilled water (Invitrogen). Residual DNA was removed from the samples by treatment with RQ1 DNase (Promega, Madison, Wis.) at 37° C. for 1 hour per the manufacturer's protocol. Samples were extracted with phenol:chloroform:isoalkyl alcohol (25:24:1) (Invitrogen) and the RNA was precipitated with 1/10 volume of 3M sodium acetate (pH=5.2) and 3 volumes of 100% ethanol. Samples were frozen at 80° C. for a minimum of 2 hours. After centrifugation, the samples were washed with 75% ethanol, air dried, and resuspended in 20 µl of UltraPure distilled water (Invitrogen) and stored at −80° C. until time of use, RNA was quantified using a NanoDrop-1000 Spectrophotometer with the program ND-1000 V3.8.1 (Thermo Fisher Scientific, Wilmington, Del.).

Reverse transcription (Improm-II Reverse Transcription System, Promega) followed by real-time PCR analysis was performed in 20 µL volumes containing 1 µl of cDNA corresponding to 40 ng of DNase-treated RNA in the RT reaction, gene specific internal primers (0.5 µM of each primer), and 1× SsoFast EvaGreen Supermix (Bio-Rad, Hercules, Calif.). The primers were synthesized by Integrated DNA Technologies (IDT, Coralville, Iowa) and have 100% sequence homology to the marine or human genome. The primer sequences are listed below in Table 1.

TABLE 1

PRIMER SEQUENCES

| Primer Name | Forward Primer (5'→3') | Reverse Primer (5'→3') |
|---|---|---|
| mGAPDH | GTGGCAAAGTGGAGATTGTTG (SEQ ID NO: 1) | CATTCTCGGCCTTGACTGTG (SEQ ID NO: 2) |
| mTNF-α | ACGTGGAACTGGCAGAAGAG (SEQ ID NO: 3) | CTCCTCCACTTGGTGGTTTG (SEQ ID NO: 4) |
| hGAPDH | TGGTCTCCTCTGACTTCAAC (SEQ ID NO: 5) | CCTGTTGCTGTAGCCAAATT (SEQ ID NO: 6) |
| hTNF-α | CAAGCCTGTAGCCCATGTTG (SEQ ID NO: 7) | AGAGGACCTGGGAGTAGATG (SEQ ID NO: 8) |

The PCR was performed using the following conditions: 95° C. for 30 sec, 40 cycles of 95° C. for 5 sec, and 57° C. for 5 sec using a CFX96 Real-Time Detection System (Bio-Rad), GAPDH was used as a housekeeping gene to normalize mRNA levels between samples. Data was analyzed using the Bio-Rad CFX Manager V1.6.541.1028 software (Bio-Rad). The calibrator in the experiments was the sample obtained from control-treated cells. Copy numbers of targeted mRNAs were expressed as ratios of GAPDH mRNA levels. Relative quantitation was determined by the comparative $C_T$ method ($\Delta\Delta C_T$ method) in which the formula is expressed as: $2^{-\Delta\Delta C_T}(1)$.

RAW cells were incubated with or without 10 mM creatinine (Sigma-Aldrich) for 24 or 48 hours. Staining was performed on cytospins which were fixed in cold acetone, air-dried, and rehydrated in phosphate buffered saline (PBS). Blocking was performed at room temperature for 20 minutes, followed by incubation with purified rat anti-mouse TNF-α antibody (BD Biosciences, San Diego, Calif.) overnight. Slides were washed with PBS, incubated with a biotinylated anti-rat IgG made in rabbit antibody (Vector Labs, Burlingame, Calif.) for 45 minutes, and washed again with PBS. Detection was performed using the ABC kit (Vector Labs) and development with 3,3'-diaminobenzidine (DAB) horse-radish peroxidase (HRP kit) (Vector Labs). Slides were washed with PBS and counter-stained with hematoxylin gills (Sigma-Aldrich). Slides were dehydrated with ethanol/xylene and then coverslipped using Permount (Fisher Scientific). Images were captured using a Nikon Eclipsei80 microscope (NY, USA) and an Infinity 2 camera and ImageJ164 imaging software.

RT-PCR data was analyzed by two-way analysis of variance (ANOVA) with a Bonferroni's post-test. P values≤0.05 were considered statistically significant.

Example 1: TNF-α mRNA Expression Following Treatment of Mouse Macrophages with Creatinine HCl As described above, the mouse macrophage cell line (RAW 264.7) was treated with 10 mM creatinine HCl. Following exposure of the cells to creatinine HCl, TNF-α mRNA expression was decreased in mouse macrophages.

FIG. 1A shows the effects of creatinine HCl treatment on TNF-α mRNA expression in mouse macrophages. FIG. 1A shows that by 10 minutes post-exposure to 10 mM creatinine HCl, TNF-α mRNA was significantly decreased to 28% as compared to the control (100%). By 20 minutes post-exposure to creatinine HCl, mRNA levels were decreased to 13% as compared to the control. At 40 minutes post-exposure to creatinine HCl, TNF-α mRNA levels in the RAW cells began to increase, and by 60 minutes post-exposure, TNF-α mRNA levels were 47% of the control. Overall, as can be seen from FIG. 1A, creatinine HCl decreased TNF-α mRNA expression in RAW 237.6 cells from 10-30 minutes post-exposure followed by an increase from 40-60 minutes post-exposure.

Cells subjected to lipopolysaccharide as a positive control resulted in a significant increase in TNF-α mRNA expression (not shown in graphs). Values represent the mean transcript level±the SEM, relative to GAPDH transcript levels. Statistical analysis was performed using a two-way ANOVA test post hoc Bonferroni, with untreated cells as the control. Data is representative of three experiments.

Example 2: TNF-α mRNA Expression Following Treatment of Human Macrophages with Creatinine HCl The human macrophage cell line (THP-1) was also treated with 10 mM creatinine Similar to the mouse macrophages, TNF-α mRNA expression was decreased in human macrophages following exposure of the cells to creatinine HCl.

Figure 1B:
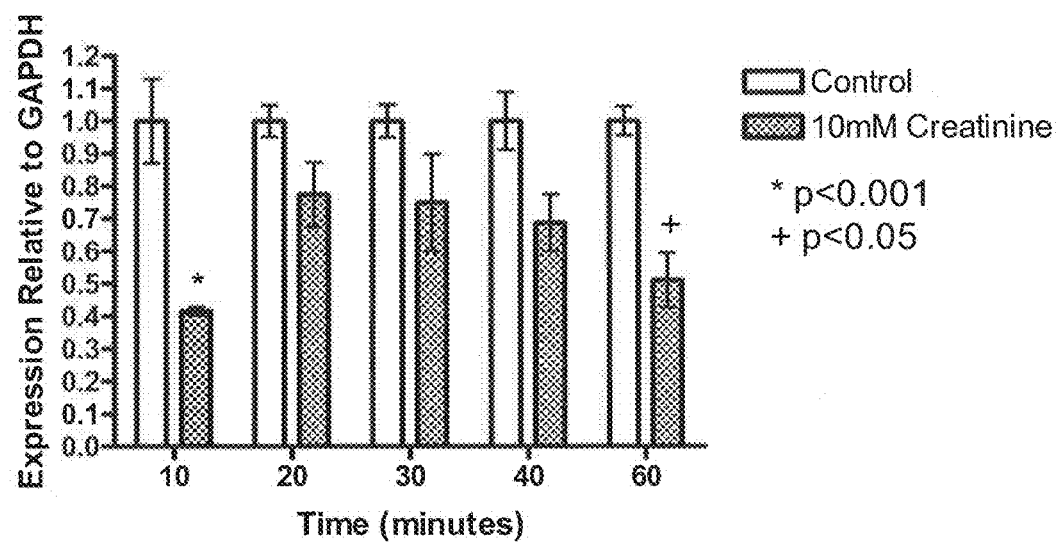
FIG. 1B is a graphical representation illustrating TNF-α mRNA expression following treatment of human macrophages with creatinine HCl.

FIG. 1B shows the effects of creatinine HCl treatment on TNF-α mRNA expression in human macrophages. As shown in FIG. 1B, by 10 minutes post-exposure to creatinine HCl, TNF-α mRNA levels were decreased to 41% of the control levels. At 20 minutes post-exposure to creatinine HCl, TNF-α mRNA levels increased; however, the mRNA levels remained below those of control-treated cells. The TNF-α mRNA levels remained steady and then dropped to 50% by 60 minutes post-exposure to creatinine HCl. Overall, as can be seen in FIG. 1B, a decrease in TNF-α mRNA expression was seen at 10 and 60 minutes with a stable expression of TNF-α from 20-40 minutes, but remained below the control.

Cells subjected to lipopolysaccharide as a positive control resulted in a significant increase in TNF-α mRNA expression (not shown in graphs). Values represent the mean transcript level±the SEM, relative to GAPDH transcript levels. Statistical analysis was performed using a two-way ANOVA test post hoc Bonferroni, with untreated cells as the control. Data is representative of three experiments.

Example 3: TNF-α mRNA Expression Following Treatment of Human T Cells with Creatinine HCl To determine whether the ability of creatinine HCl to decrease TNF-α mRNA expression is restricted to macrophage cell lines, the human T cell line (Jurkat clone E.6) was also treated with 10 mM of creatinine HCl. Following exposure of the cells to creatinine HCl, TNF-α mRNA expression was decreased in human T cells.

Figure 2:
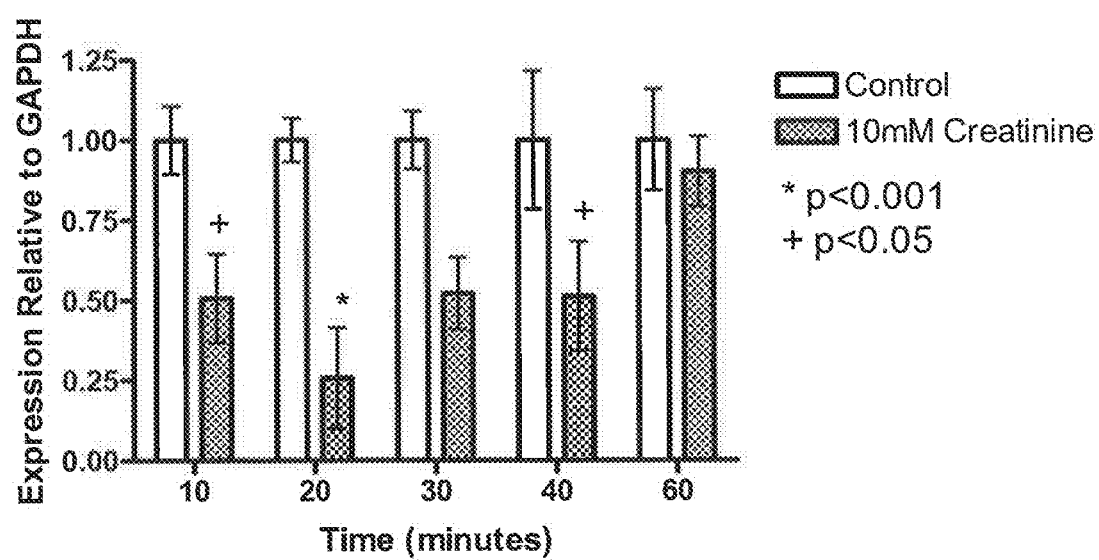
FIG. 2 is a graphical representation illustrating TNF-α mRNA expression following treatment of human T cells with creatinine HCl.

FIG. 2 shows the effects of creatinine HCl treatment on TNF-α mRNA expression in the human T cells. As demonstrated in FIG. 2, within 10 minutes of exposure to creatinine TNF-α mRNA levels dropped to 50% compared to the levels of control. By 20 minutes post-exposure to creatinine HCl, TNF-α mRNA levels decreased to their lowest levels (i.e., 25% of the control level). TNF-α mRNA levels began increasing at 30 minutes post-exposure to creatinine HCl, and continued to increase to control levels by 60 minutes post-exposure. Indeed, as can be seen from FIG. 2, creatinine HCl exposure decreased TNF-α mRNA expression in the human T cells from 10-40 minutes post-exposure with a return to baseline expression by 60 minutes post-exposure.

Cells subjected to lipopolysaccharide as a positive control resulted in a significant increase in TNF-α mRNA expression (not shown in graphs). Values represent the mean transcript level±the SEM, relative to GAPDH transcript levels. Statistical analysis was performed using a two-way ANOVA test post hoc Bonferroni, with untreated cells as the control. Data is representative of three experiments.

Example 4: TNF-α Protein Expression Following Treatment of Mouse Macrophages with Creatinine HCl and Creatine Monohydrate Treatment with Creatinine HCl To determine whether alterations in TNF-α mRNA expression after creatinine exposure resulted in alterations in TNF-α protein expression, immunohistochemical staining of the mouse macrophage cells (RAW 264.7) was performed following incubation with 10 mM of creatinine HCl for 24 and 48 hours.

Figure 3A:
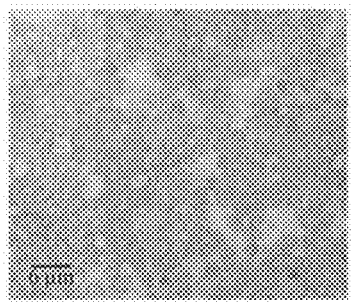
FIGS. 3A-D illustrate immunohistochemical staining of TNF-α protein expression following exposure of mouse macrophages with or without creatinine HCl.
Figure 3B:
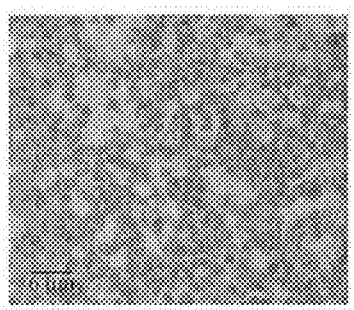
Figure 3C:
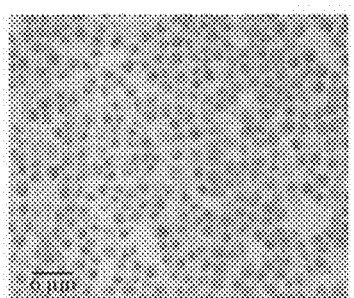
Figure 3D:
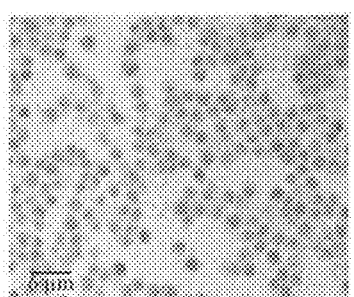

FIGS. 3A-D demonstrate the effects of creatinine HCl exposure on TNF-α protein expression in mouse macrophage cells through the use of immunohistochemical staining. For comparison purposes, FIG. 3A shows the control-treated RAW cells and FIG. 3B shows staining without exposure to creatinine HCl. FIGS. 3C and 3D show immunohistochemical staining of the mouse macrophage cells following incubation with 10 mM of creatinine HCl for 24 and 48 hours, respectively. As shown in FIGS. 3C and 3D, the RAW cells displayed lower signals as compared to the control-treated RAW cells at 24 and 48 hours post-incubation with creatinine HCL, respectively. This finding was consistent with RT-PCR studies demonstrating that TNF-α mRNA expression decreases following exposure of creatinine HCL.

Treatment with Creatine Monohydrate

To determine whether alterations in TNF-α mRNA expression after creatine monohydrate exposure resulted in alterations in TNF-α protein expression, immunohistochemical staining of the mouse macrophage cells (RAW 264.7) was also performed following incubation with 10 mM creatine monohydrate for 24 and 48 hours.

Figure 3E:
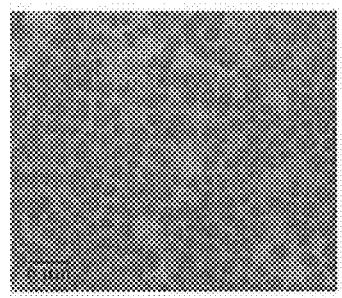
FIGS. 3E-H illustrate immunohistochemical staining of TNF-α protein expression following exposure of mouse macrophages with or without creatine monohydrate.
Figure 3F:
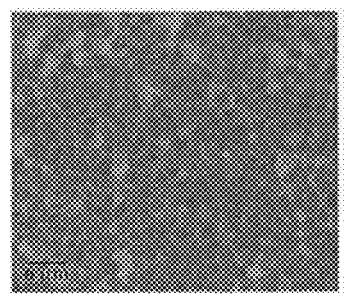
Figure 3G:
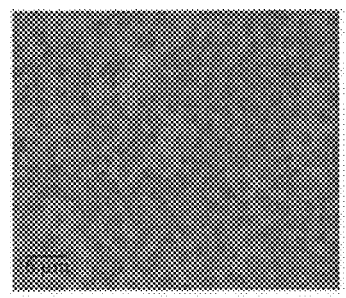
Figure 3H:
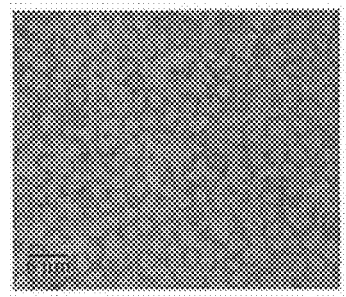

FIGS. 3E-H demonstrate the effects of creatine monohydrate exposure on TNF-α protein expression in mouse macrophage cells through the use of immunohistochemical staining. For comparison purposes, FIG. 3E shows the control-treated RAW cells and FIG. 3F shows staining without exposure to creatine monohydrate. FIGS. 3G and 3H show immunohistochemical staining of the mouse macrophage cells following incubation with 10 mM of creatine monohydrate for 24 and 48 hours, respectively. As shown in the immunohistochemical stains of FIGS. 3G and 3H, treatment of creatine monohydrate for 24 and 48 hours showed a similar reduction in TNF-α signal as compared with the creatinine HCl treatment.

In sum, immunohistochemical staining revealed a decrease of TNF-α signal in mouse macrophage cells after 24 and 48 hours post-exposure to creatinine HCl. Similarly, the immunohistochemical staining revealed a decrease of TNF-α signal in mouse macrophage cells after 24 and 48 hours post-exposure of creatine monohydrate. Without being bound by any particular theory, it is believed that the decrease in TNF-α signal following treatment with creature monohydrate is due to the quick hydrolyzation of creatine into creatinine (e.g., within 20-70 minutes).

In sum, creatinine HCl effectively reduces TNF-α mRNA levels compared to untreated control levels in all three cell lines. Together, these results determine that creatinine HCl acts as an anti-inflammatory immunomodulator in vitro on both human and mouse cell lines.

Although the present invention has been described with reference to particular embodiments, it will be understood to those skilled in the art that the invention is capable of a variety of alternative embodiments within the spirit of the appended claims. For example, the present invention is also contemplated for use as a preventative treatment to attenuate the effects of inflammation.

What is claimed is:

1. A method for treating rheumatoid arthritis, osteoarthritis, psoriatic arthritis, multiple sclerosis, or inflammatory bowel disease in a patient, comprising:
    administering an effective amount of an anti-inflammatory agent to the patient, wherein the anti-inflammatory agent comprises a creatinine salt or its precursors, and wherein levels of tumor necrosis factor alpha in the patient are reduced by at least 40 percent when compared to levels prior to administration of the anti-inflammatory agent.

2. The method of claim 1, wherein the anti-inflammatory agent is administered to the patient as a topical formulation.

3. The method of claim 2, wherein the topical formulation comprises the anti-inflammatory agent in an amount of about 10 percent by weight to about 40 percent by weight.

4. The method of claim 1, wherein the creatinine salt is creatinine hydrochloride.

5. The method of claim 1, wherein the anti-inflammatory agent is administered in conjunction with at least one other compound selected from the group consisting of a homeopathic compound, a co-medication, a nutraceutical, a plant extract, a herbal preparation, a cosmetic agent, a pharmaceutical, or combinations thereof.

6. A method for treating inflammation associated with rheumatoid arthritis, osteoarthritis, psoriatic arthritis, or multiple sclerosis in a patient, comprising:
    administering a topical formulation to an inflamed area of the patient, wherein the topical formulation comprises an effective amount of creatinine hydrochloride.

7. The method of claim 6, wherein the effective amount of creatinine hydrochloride is about 10 percent by weight to about 40 percent by weight.

8. The method of claim 6, wherein the effective amount of creatinine hydrochloride is about 15 percent by weight to about 35 percent by weight.

9. The method of claim 6, wherein the topical formulation is an ointment, lotion, cream, gel, adhesive patch, or a wrap.

10. The method of claim 9, wherein the adhesive patch or wrap comprises a controlled release system for administration of the topical formulation.

\* \* \* \* \*